US011500858B2

(12) United States Patent
Asif et al.

(10) Patent No.: US 11,500,858 B2
(45) Date of Patent: Nov. 15, 2022

(54) GENERATING THREE-DIMENSIONAL SPIKES USING LOW-POWER COMPUTING HARDWARE

(71) Applicant: International Business Machines Corporation, Armonk, NY (US)

(72) Inventors: Umar Asif, Melbourne (AU); Subhrajit Roy, Melbourne (AU); Jianbin Tang, Doncaster East (AU); Stefan Harrer, Hampton (AU)

(73) Assignee: International Business Machines Corporation, Armonk, NY (US)

( * ) Notice: Subject to any disclaimer, the term of this patent is extended or adjusted under 35 U.S.C. 154(b) by 279 days.

(21) Appl. No.: 16/842,921

(22) Filed: Apr. 8, 2020

(65) Prior Publication Data
US 2021/0319009 A1 Oct. 14, 2021

(51) Int. Cl.
*G06F 16/23* (2019.01)
*G06N 3/04* (2006.01)
(Continued)

(52) U.S. Cl.
CPC ........ *G06F 16/2379* (2019.01); *A61B 5/7264* (2013.01); *G06K 9/6289* (2013.01);
(Continued)

(58) Field of Classification Search
None
See application file for complete search history.

(56) References Cited

U.S. PATENT DOCUMENTS

| | | | |
|---|---|---|---|
| 8,248,839 B2 * | 8/2012 | George | H03K 5/00 365/189.09 |
| 9,082,079 B1 | 7/2015 | Coenen | |

(Continued)

FOREIGN PATENT DOCUMENTS

| | | |
|---|---|---|
| CN | 108805797 A | 11/2018 |
| CN | 109766945 A | 5/2019 |
| EP | 3716020 A1 | 9/2020 |

OTHER PUBLICATIONS

Chen, Huan-Yuan & Chen, Chih-Chang & Hwang, Wen-Jyi. (2017). An Efficient Hardware Circuit for Spike Sorting Based on Competitive Learning Networks. Sensors. 17.2232. 10.3390/s17102232.
(Continued)

*Primary Examiner* — Santiago Garcia
(74) *Attorney, Agent, or Firm* — Patterson + Sheridan, LLP

(57) ABSTRACT

Aspects described herein include a method of generating three-dimensional (3D) spikes. The method comprises receiving a signal comprising time-series data and generating a first two-dimensional (2D) grid. Generating the first 2D grid comprises mapping segments of the time-series data to respective positions of the first 2D grid, and generating, for each position, a spike train corresponding to the respective mapped segment. The method further comprises generating a second 2D grid including performing, for each position, a mathematical operation on the spike train of the corresponding position of the first 2D grid. The method further comprises generating a third 2D grid including performing spatial filtering on the positions of the second 2D grid. The method further comprises generating a 3D grid based on a combination of the first 2D grid, the second 2D grid, and the third 2D grid. The 3D grid comprises one or more 3D spikes.

19 Claims, 4 Drawing Sheets

(51) Int. Cl.
*A61B 5/00* (2006.01)
*G06K 9/62* (2022.01)
*G06N 20/00* (2019.01)
*A61B 5/24* (2021.01)

(52) U.S. Cl.
CPC ............... *G06N 3/049* (2013.01); *A61B 5/24* (2021.01); *G06N 20/00* (2019.01)

(56) References Cited

U.S. PATENT DOCUMENTS

| | | | |
|---|---|---|---|
| 9,189,730 | B1 | 11/2015 | Coenen et al. |
| 10,234,942 | B2 | 3/2019 | Connor |
| 2004/0075659 | A1* | 4/2004 | Taubin ................ G06T 17/20 345/428 |
| 2005/0071306 | A1* | 3/2005 | Kruszewski ............ A63F 13/10 345/473 |
| 2005/0078861 | A1* | 4/2005 | Usikov ................ G06T 11/006 382/154 |
| 2014/0362091 | A1* | 12/2014 | Bouaziz ............... G06V 40/176 345/473 |
| 2016/0208213 | A1* | 7/2016 | Doyle ................... B06B 1/0223 |
| 2017/0148192 | A1* | 5/2017 | Bauer .................. G06T 7/0012 |
| 2018/0322365 | A1 | 11/2018 | Yehezkel Rohekar |
| 2021/0272358 | A1* | 9/2021 | Stevens ............... G06V 20/647 |

OTHER PUBLICATIONS

Kexin Rong and Peter Pailis, "ASAP: Prioritizing Attention via Time Series Smoothing," Sumbitted on Mar. 2, 2017, Proc. VLDB Endow. vol. 10, No. 11 pp. 1358-1369, 2017, DOI:10.14778/3137628. 3137645.

PCT, International Search Report and Written Opinion for Application PCT/IB2021/052310 dated Jun. 24, 2021.

Authors et al., "Automatically Scaling Multi-Tenant Machine Learning" IP.com, dated Dec. 15, 2017, pp. 1-35.

Authors et al., "Identifying Energy Overconsumption Based on Ambient Noise Audio Signatures," IP.com, dated Dec. 13, 2017, pp. 1-37.

Authors et al., "Machine Learning for Hardware Simulation," IP.com, dated Dec. 13, 2017, pp. 1-33.

* cited by examiner

GENERATING THREE-DIMENSIONAL SPIKES USING LOW-POWER COMPUTING HARDWARE

BACKGROUND

The present disclosure relates to transformation of time-series data for machine learning, and more specifically, to generating three-dimensional spikes using low-power computing hardware.

Time-series data, such as raw sensor data, is often transformed into a suitable representation before being provided to a machine learning (ML) algorithm. However, the transformation can be computationally intensive, requiring relatively large amounts of power and memory. In this way, performing the transformation may be not suitable for ML modules having low-power computing hardware.

SUMMARY

According to one embodiment, a method of generating three-dimensional (3D) spikes comprises receiving a signal comprising time-series data, and generating a first two-dimensional (2D) grid. Generating the first 2D grid comprises mapping segments of the time-series data to respective positions of the first 2D grid, and generating, for each position of the first 2D grid, a spike train corresponding to the respective mapped segment. The method further comprises generating a second 2D grid. Generating the second 2D grid comprises performing, for each position of the second 2D grid, a mathematical operation on the spike train of the corresponding position of the first 2D grid. The method further comprises generating a third 2D grid. Generating the third 2D grid comprises performing spatial filtering on the positions of the second 2D grid. The method further comprises generating a 3D grid based on a combination of the first 2D grid, the second 2D grid, and the third 2D grid. The 3D grid comprises one or more 3D spikes.

According to one embodiment, a computer processor comprises a segmenter configured to receive a signal comprising time-series data, and map segments of the time-series data to respective positions of a first two-dimensional (2D) grid. The computer processor further comprises a spike generator configured to generate, for each position of the first 2D grid, a spike train corresponding to the respective mapped segment. The computer processor further comprises a mathematical operator configured to perform, for each position of a second 2D grid, a mathematical operation on the spike train of the corresponding position of the first 2D grid. The computer processor further comprises a spatial filter configured to generate a third 2D grid by performing spatial filtering on the second 2D grid. The computer processor further comprises a 3D grid generator configured to generate a 3D grid based on a combination of the first 2D grid, the second 2D grid, and the third 2D grid, wherein the 3D grid comprises one or more 3D spikes.

According to one embodiment, a method comprises generating, for each position of a first two-dimensional (2D) grid, a spike train corresponding to a respective segment of time-series data mapped to the position. The method further comprises performing, for each position of a second 2D grid, a mathematical operation on the spike train of the corresponding position of the first 2D grid. The method further comprises performing spatial filtering on the positions of the second 2D grid to generate a third 2D grid. The method further comprises generating a 3D grid based on a combination of the first 2D grid, the second 2D grid, and the third 2D grid, wherein the 3D grid comprises one or more 3D spikes.

DETAILED DESCRIPTION

Figure 1:
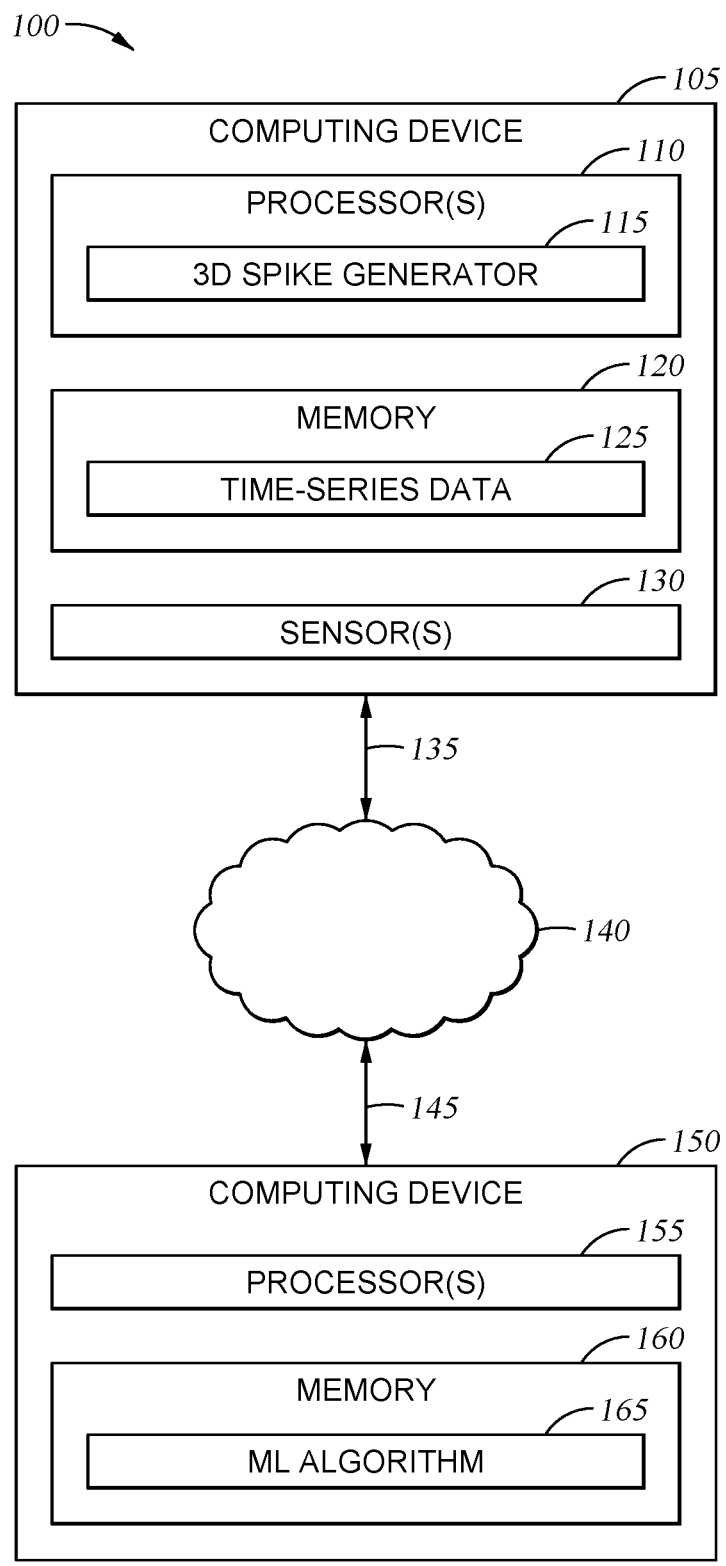
FIG. 1 is a block diagram illustrating an exemplary system having a three-dimensional (3D) spike generator, according to one or more embodiments.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system."

Various machine learning (ML) algorithms operate on time-series data, which may be first transformed into a representation that is suitable for the particular ML algorithm. In some cases, the time-series data is transformed into a more discriminative format that yields improved performance by the ML algorithm. For example, transforming the time-series data into a two-dimensional (2D) representation based on Laplacian methods has been shown to yield improved ML performance. However, the transformation can be computationally intensive, requiring relatively large amounts of power and memory. In this way, performing the transformation may be not suitable for ML modules having low-power computing hardware.

Embodiments herein are directed to power-efficient implementations for generating three-dimensional (3D) spikes using spike trains. In some embodiments, Laplacian computations are performed in a multidimensional spike domain to generate the 3D spikes using minimal computing hardware, offering comparable accuracy and discriminative capability as digital signal processor (DSP)-based systems while requiring significantly less power and computing resources.

In some embodiments, the time-series data is segmented into a plurality of segments that are processed by a 2D array of voltage-spike (VS) converters. In some embodiments, spatio-temporal gradients are computed for each node of the 2D array using spatially neighboring nodes.

FIG. 1 is a block diagram illustrating an exemplary system 100 having a three-dimensional (3D) spike generator, according to one or more embodiments. The system 100 comprises a computing device 105 communicatively coupled with a computing device 150 via a network 140.

The computing device 105 comprises one or more computer processors 110 (also referred to as "processors 110") and a memory 120. The one or more processors 110 may be implemented in any suitable form, such as a general purpose microprocessor, a controller, an application-specific integrated circuit (ASIC), and so forth. The memory 120 may include a variety of computer-readable media selected for their size, relative performance, or other capabilities: volatile and/or non-volatile media, removable and/or non-removable media, etc.

The computing device 105 further comprises one or more sensors 130 of any suitable type(s). In some embodiments, the one or more sensors 130 comprise biometric sensors such as a heart rate sensor, a blood pressure sensor, a motion sensor (e.g., an inertial measurement unit (IMU)), and so forth. The one or more sensors 130 generate time-series data 125 that may be stored in the memory 120. The time-series data 125 may have any suitable format, such as biometric data (heart rate data, blood pressure data, step data, stair data, and so forth).

In some embodiments, the memory 120 is dimensioned to store only a portion of the time-series data 125 at any particular time, e.g., corresponding to a length of time. For example, the memory 120 may be dimensioned to store thirty minutes, one hour, twelve hours, etc. of time-series data 125.

A 3D spike generator 115 receives the time-series data 125 and generates one or more 3D spikes. Generally, the one or more 3D spikes provides a representation of the time-series data 125 with a more discriminative encoding, and with more robustness to spatial noise than, e.g., one-dimensional (1D) spike trains. In some embodiments, the one or more 3D spikes comprise 3D Laplacian spikes. In some embodiments, the 3D spike generator 115 is implemented as a distinct processor of the one or more processors 110. In other embodiments, the 3D spike generator 115 is implemented as logic within the one or more processors 110, e.g., hardware and/or firmware.

The computing device 105 communicates the one or more 3D spikes to a computing device 150 via the network 140. The computing devices 105, 150 are connected via respective communicative links 135, 145 to the network 140. The network 140 may represent one or more networks of any suitable type(s) for communicatively coupling the computing devices 105, 150. For example, the network 140 may comprise the Internet, a local area network (LAN), a wide area network (WAN), and/or a wireless network. Each of the communicative links 135, 145 may have any suitable implementation, such as copper transmission cables, optical transmission fibers, wireless transmission, routers, firewalls, switches, gateway computers, and/or edge servers.

The computing device 150 comprises one or more computer processors 155 and a memory 160. The one or more computer processors 155 may be configured similarly to the one or more processors 110, and the memory 160 may be configured similarly to the memory 120. The memory 160 comprises a ML algorithm 165 that operates on the one or more 3D spikes generated by the 3D spike generator 115. In some embodiments, the ML algorithm 165 is implemented as program code executed by the one or more computer processors 155. In this way, the 3D spike generator 115 acts as a pre-processor for the ML algorithm 165. The ML algorithm 165 may be of any suitable type, such as supervised learning algorithms, unsupervised learning algorithms, and reinforcement learning algorithms. Some non-limiting examples of the ML algorithm 165 include Linear Regression, Logistic Regression, Decision Tree, Support Vector Machine (SVM), Naive Bayes, k-Nearest Neighbors (kNN), K-Means, Random Forest, Dimensionality Reduction Algorithms, and Gradient Boosting algorithms.

Thus, the generated 3D spikes can be used with "traditional" machine learning algorithms and with deep learning models. For machine learning algorithms such as SVM, K-means, Random Forests, kNN, and Recurrent Neural Networks such as Long Short Term Memory (LSTM) networks, the individual channels of 3D spikes can be concatenated into a linear data structure and fed into the algorithms for machine learning. 3D Convolutional Neural Networks (3D CNNs) represent one example of a ML algorithm that is particularly well-suited for processing 3D spikes, as 3D CNNs use 3D filters which can directly process 3D spikes data representation without any pre-processing. Another well-suited machine learning algorithm is a combination of 3D CNN and an LSTM. There, a backbone 3D CNN acts as a feature extractor to produce features from the 3D spikes, and the LSTM uses these features to learn temporal information in the features at different temporal resolutions.

Each of the computing devices 105, 150 may have any suitable implementation, such as a desktop computing device, a mobile computing device (e.g., laptop, smartphone, tablet), and a wearable computing device (e.g., smart watch, smart ring, smart glasses, activity monitor).

In some embodiments, the computing device 105 has limited computing resources and/or power consumption relative to the computing device 150. For example, the computing device 105 may be implemented as a battery-powered wearable computing device, and the computing device 150 may be implemented as a desktop computing device or mobile computing device having significantly greater computing resources and/or power consumption. Thus, implementing the 3D spike generator 115 in the one or more processors 110 using limited hardware, and implementing the ML algorithm 165 on the computing device 150, enables use of a low-power implementation of the computing device 105.

Although the ML algorithm 165 is depicted as separate from the computing device 105 in the system 100, alternate implementations of the computing device 105 may include the ML algorithm 165, e.g., as program code in the memory 120 that is executed by the one or more computer processors 110. In such alternate implementations, the computing device 105 may still achieve computing resources and/or power savings through use of the 3D spike generator 115, when compared with DSP-based implementations.

In one exemplary sequence, the 3D spike generator 115 receives a signal from the one or more sensors 130 comprising the time-series data 125. The 3D spike generator 115 generates a first 2D grid, which comprises mapping segments of the time-series data 125 to respective positions of the first 2D grid and generating, for each position of the first 2D grid, a spike train corresponding to the respective mapped segment. The 3D spike generator 115 generates a second 2D grid, which comprises performing, for each position of the second 2D grid, a mathematical operation on the spike train of the corresponding position of the first 2D grid. The 3D spike generator 115 generates a third 2D grid, which comprises performing spatial filtering on the positions of the second 2D grid. The 3D spike generator 115 generates a 3D grid based on a combination of the first 2D grid, the second 2D grid, and the third 2D grid. The 3D grid comprises one or more 3D spikes.

Thus, the one or more 3D spikes represent 1D spike trains that have been packed into a 3D data structure and combined with spatiotemporal gradients from the time-series data 125. The spatiotemporal gradients are estimated using spatial neighbors in a multi-dimensional grid structure and represent a holistic view of the time-series data 125. An exemplary hardware-based implementation of the 3D spike generator is described below with respect to FIG. 4.

Figure 2:
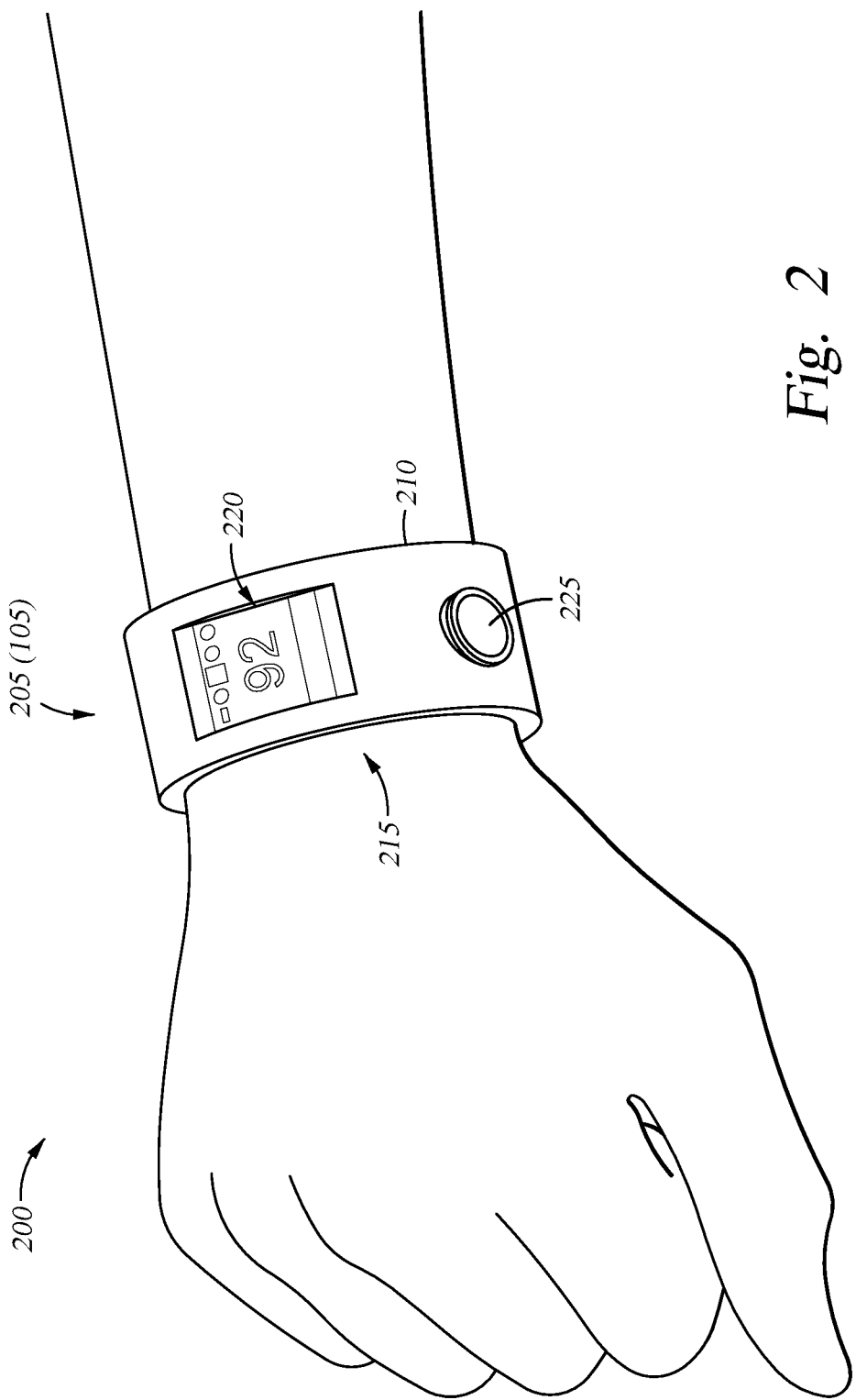
FIG. 2 is a diagram illustrating an exemplary low-power computing device, according to one or more embodiments.

FIG. 2 is a diagram 200 illustrating an exemplary low-power computing device, according to one or more embodiments. The features depicted in the diagram 200 may be used in conjunction with other embodiments. For example, a wearable computing device 205 represents one example of the computing device 105 of FIG. 1.

As shown in the diagram 200, the wearable computing device 205 is implemented as a smart watch or an activity monitor. The wearable computing device 205 comprises a wristband 210 that extends around a wrist 215 of a wearer. The wristband 210 may include a buckle or clasp that secures the wearable computing device 205 around the wrist 215.

The wearable computing device 205 further comprises a display 220 connected with the wristband 210. The display 220 may be implemented using any suitable display technology, such as a liquid crystal display (LCD), an organic light-emitting diode (OLED), and so forth. The processor(s) included in the wearable computing device 205 may receive biometric data acquired using one or more sensors of the wearable computing device 205, and may communicate the biometric data to be displayed using the display 220.

The wearable computing device 205 further comprises one or more input devices, such as a button 225 that is pressed by the wearer to navigate the display 220, to change the information displayed using the display 220, and so forth.

In some embodiments, the processor(s) of wearable computing device 205 generate one or more 3D spikes corresponding to time-series data received from the one or more sensors. The wearable computing device 205 may communicate the one or more 3D spikes to an external computing device using a wired or wireless interface.

Figure 3:
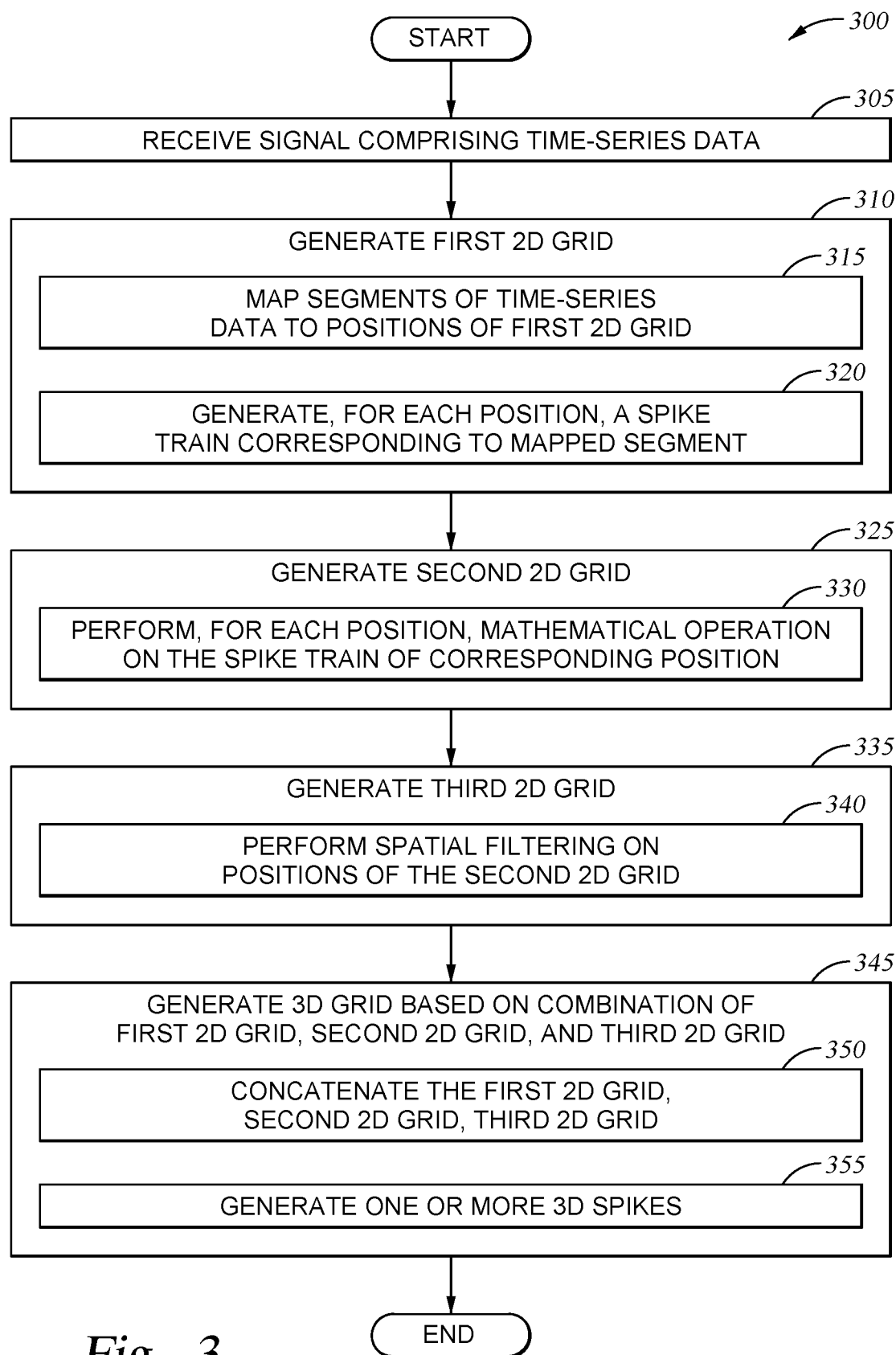
FIG. 3 is an exemplary method of generating a 3D grid having one or more 3D spikes, according to one or more embodiments.

FIG. 3 is an exemplary method 300 of generating a 3D grid having one or more 3D spikes, according to one or more embodiments. The method 300 may be used in conjunction with other embodiments. For example, the method 300 may be performed by the 3D spike generator 115 of FIG. 1.

The method 300 begins at block 305, where the 3D spike generator receives a signal comprising time-series data. At block 310, the 3D spike generator generates a first 2D grid. In some embodiments, generating the first 2D grid comprises mapping segments of time-series data to positions of the first 2D grid (block 315), and for each position of the first 2D grid, generating a spike train corresponding to the mapped segment (block 320).

At block 325, the 3D spike generator generates a second 2D grid. In some embodiments, generating the second 2D grid comprises performing, for each position of the second 2D grid, a mathematical operation on the spike train of the corresponding position of the first 2D grid (block 330). In some embodiments, the mathematical operation comprises a Laplacian operation, which may include calculating gradients and summing the gradients. Other types of mathematical operations are also contemplated, such as performing a sine or cosine operation on the spike train.

In some embodiments, the Laplacian operation is performed using a single pass through the time-series data, instead of looping through the time-series data multiple times to determine the neighbor information for each position of the second 2D grid. In this way, the 3D spike generator may be implemented with a smaller memory (as less of the time-series is data is required to be stored) and the Laplacian operation may be performed more quickly.

At block 335, the 3D spike generator generates a third 2D grid. In some embodiments, generating the third 2D grid comprising performing spatial filtering on positions of the second 2D grid (block 340). The spatial filtering may remove high-frequency artifacts after the Laplacian operation.

At block 345, the 3D spike generator generates a 3D grid based on a combination of the first 2D grid, the second 2D grid, and the third 2D grid. In some embodiments, generating the 3D grid comprises concatenating the first 2D grid, the second 2D grid, and the third 2D grid (block 350). In some embodiments, generating the 3D grid comprises generating one or more 3D spikes (block 355). The method 300 ends following completion of the block 345.

Figure 4:
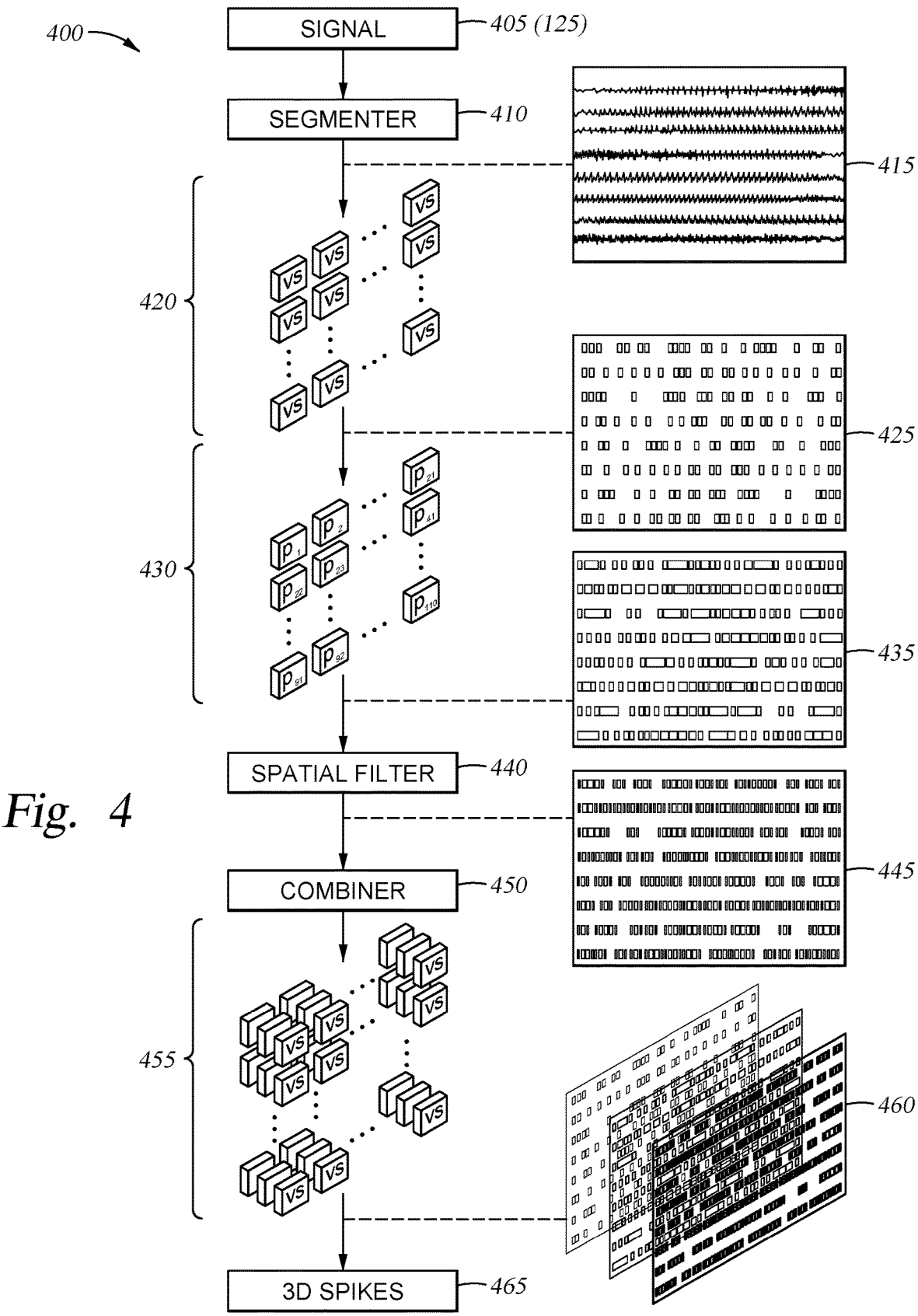
FIG. 4 is a diagram illustrating generating a 3D grid having one or more 3D spikes, according to one or more embodiments.

FIG. 4 is a diagram 400 illustrating generating a 3D grid having one or more 3D spikes, according to one or more embodiments. The features depicted in the diagram 400 may be used in conjunction with other embodiments. For example, the diagram 400 represents an exemplary hardware-based implementation of the 3D spike generator 115 of FIG. 1.

In the diagram 400, a signal 405 comprising the time-series data 125 is received at a segmenter 410. In some embodiments, the signal 405 is received from a sensor. The segmenter 410 generates segments 415 of the time-series data 125 using spatiotemporal windows. In some embodiments, the segmenter 410 segments the time-series data 125 at regular intervals (e.g., the spatiotemporal windows are a same size and the segments 415 are all a same length). In other embodiments, the segmenter 410 segments the time-series data 125 at different intervals (e.g., the spatiotemporal windows may have different sizes and the segments 415 may have different lengths). Regardless of whether the spatiotemporal windows are same-sized or differently-sized, the segments 415 of the time-series data 125 may be partly overlapping or non-overlapping with each other. The architecture of the segmenter 410 may generally be the same for both fixed-length and variable-length segments. In some embodiments, an optimal window-size parameter and a window-overlap parameter is determined through a hyperparameter search on a range of parameter values and selecting the parameters which produce the best model performance.

The segmenter 410 also maps (or routes) the segments 415 of the time-series data 125 to respective positions of a first 2D grid. The first 2D grid may have any suitable dimensioning. In some embodiments, the segments 415 are provided to a spike generator 420 that generates, for each position of the first 2D grid, a spike train corresponding to the respective mapped segment 415. As shown, the spike generator 420 comprises a 2D array of voltage-spike (VS) converters, and each position of the first 2D grid corresponds to a respective VS converter of the 2D array that generates the respective spike train. Thus, the spike generator 420 generates spike trains 425 in a 2D spatial domain.

In some embodiments, the 3D spike generator comprises a memory that stores the first 2D grid (i.e., the spike trains 425 of the first 2D grid), and a 3D grid generator accesses the first 2D grid from the memory. In some embodiments, the memory comprises an accumulator, although other types of memory are also contemplated.

In some embodiments, the spike trains 425 of the first 2D grid may be smoothed by being passed through a filter. Regardless of whether the spike trains 425 are filtered, a second 2D grid is generated using the spike trains 425 of the first 2D grid. In some embodiments, generating the second 2D grid comprises performing, for each position of the second 2D grid, a mathematical operation on the spike train 425 of the corresponding position of the first 2D grid. Some examples of the mathematical operation include a Laplacian operation, a sine or cosine operation, and so forth.

Using the example of the Laplacian operation, the spike trains 425 are provided to a 2D differential array 430 that computes spatial gradients 435, which may be passed through a router and a summer to sum the spatial gradients 435 over the required indices to generate Laplacians. For example, for a particular position of the first 2D grid, neighboring position(s) in a first dimension and neighboring position(s) in a second dimension are used to compute directional differentials in the first dimension and in the second dimension that are summed.

A third 2D grid is generated using the spatial gradients 435. In some embodiments, a spatial filter 440 removes high-frequency artifacts from the Laplacians to generate the third 2D grid (as filtered spike trains 445). For example, the spatial filter 440 may average the values of the neighboring positions in the first dimension and the second dimension to smooth the spatial gradients 435. Thus, generating the third 2D grid comprises performing spatial filtering on the positions of the second 2D grid.

A 3D grid generator generates a 3D grid 460 based on a combination of the first 2D grid, the second 2D grid, and the third 2D grid. The 3D grid 460 comprises one or more 3D spikes 465, In some embodiments, the 3D grid generator concatenates the first 2D grid, the second 2D grid, and the third 2D grid to generate the 3D grid 460. In some embodiments, the 3D grid generator comprises a 3D array of VS converters. A respective VS converter of the 3D array generates the one or more 3D spikes 465 for the corresponding position of the 3D grid 460.

Thus, according to the implementation shown in the diagram 400, the 3D spike generator may be implemented using minimal hardware components to generate 3D spike trains (e.g., Laplacians) in a power-efficient manner. To achieve this, the 3D spike generator uses arrays of VS converters arranged in a multi-dimensional grid structure. The 3D spike generator splits the time-series data into multiple segments, distributes the segments among the individual VS converters, and uses neighbor information from the multi-dimensional grid structure to compute spatiotemporal gradients for the 3D spikes.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present disclosure, other and further embodiments of the disclosure may be devised without departing from the basic scope thereof, and the scope thereof is determined by the claims that follow.

What is claimed is:

1. A method of generating three-dimensional (3D) spikes, the method comprising:
    receiving a signal comprising time-series data;
    generating a first two-dimensional (2D) grid, wherein generating the first 2D grid comprises:
        mapping segments of the time-series data to respective positions of the first 2D grid; and
        generating, for each position of the first 2D grid, a spike train corresponding to the respective mapped segment;
    generating a second 2D grid, wherein generating the second 2D grid comprises performing, for each position of the second 2D grid, a mathematical operation on the spike train of the corresponding position of the first 2D grid;
    generating a third 2D grid, wherein generating the third 2D grid comprises performing spatial filtering on the positions of the second 2D grid; and
    generating a 3D grid based on a combination of the first 2D grid, the second 2D grid, and the third 2D grid, wherein the 3D grid comprises one or more 3D spikes, and wherein, for each position of the 3D grid, a respective voltage-spike (VS) converter of a 3D array of VS converters generates the one or more 3D spikes.

2. The method of claim 1, wherein the mathematical operation comprises a Laplacian operation.

3. The method of claim 2, wherein the Laplacian operation is performed using a single pass through the time-series data.

4. The method of claim 1, further comprising:
    segmenting the time-series data at regular intervals.

5. The method of claim 1, wherein the segments of the time-series data are partly overlapping.

6. The method of claim 1, wherein generating the 3D grid comprises:
    concatenating the first 2D grid, the second 2D grid, and the third 2D grid; and
    generating the one or more 3D spikes.

7. The method of claim 6, wherein, for each position of the first 2D grid, a respective VS converter of a 2D array of VS converters generates the respective spike train.

8. A computer processor comprising:
    a segmenter configured to:
        receive a signal comprising time-series data; and
        map segments of the time-series data to respective positions of a first two-dimensional (2D) grid;
    a spike generator configured to generate, for each position of the first 2D grid, a spike train corresponding to the respective mapped segment;
    a mathematical operator configured to perform, for each position of a second 2D grid, a mathematical operation on the spike train of the corresponding position of the first 2D grid;
    a spatial filter configured to generate a third 2D grid by performing spatial filtering on the second 2D grid; and
    a 3D grid generator configured to generate a 3D grid based on a combination of the first 2D grid, the second 2D grid, and the third 2D grid, wherein the 3D grid comprises one or more 3D spikes, and wherein, for each position of the 3D grid, a respective voltage-spike (VS) converter of a 3D array of VS converters generates the one or more 3D spikes.

9. The computer processor of claim 8,
wherein the spike generator comprises a 2D array of VS converters, and
wherein, for each position of the first 2D grid, a respective VS converter of the 2D array generates the respective spike train.

10. The computer processor of claim 9, further comprising:
a memory coupled with the VS converters of the 2D array, the memory configured to store the first 2D grid,
wherein the 3D grid generator accesses the first 2D grid from the memory.

11. The computer processor of claim 10, wherein the memory comprises an accumulator, the computer processor further comprising:
a filter arranged between the accumulator and the mathematical operator.

12. The computer processor of claim 8, wherein the mathematical operator is a Laplacian operator comprising:
a plurality of differential operators, each differential operator corresponding to a respective position of the second 2D grid; and
a summer.

13. The computer processor of claim 11, wherein the Laplacian operator is configured to perform a Laplacian operation using a single pass through the time-series data.

14. The computer processor of claim 8, wherein the segmenter is configured to:
segment the time-series data at regular intervals.

15. The computer processor of claim 8, wherein the segments of the time-series data are partly overlapping.

16. A method comprising:
generating, for each position of a first two-dimensional (2D) grid, a spike train corresponding to a respective segment of time-series data mapped to the position;
performing, for each position of a second 2D grid, a mathematical operation on the spike train of the corresponding position of the first 2D grid;
performing spatial filtering on the positions of the second 2D grid to generate a third 2D grid; and
generating a 3D grid based on a combination of the first 2D grid, the second 2D grid, and the third 2D grid, wherein the 3D grid comprises one or more 3D spikes, and wherein, for each position of the 3D grid, a respective voltage-spike (VS) converter of a 3D array of VS converters generates the one or more 3D spikes.

17. The method of claim 16,
wherein, for each position of the first 2D grid, a respective VS converter of a 2D array of VS converters generates the respective spike train.

18. The method of claim 16, wherein the mathematical operation comprises a Laplacian operation.

19. The method of claim 16, wherein the segments of the time-series data are partly overlapping.

* * * * *